(12) United States Patent
Hoffman

(10) Patent No.: US 7,187,748 B2
(45) Date of Patent: Mar. 6, 2007

(54) MULTIDETECTOR CT IMAGING METHOD AND APPARATUS WITH REDUCING RADIATION SCATTERING

(75) Inventor: David Michael Hoffman, New Berlin, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 302 days.

(21) Appl. No.: 10/748,612

(22) Filed: Dec. 30, 2003

(65) Prior Publication Data

US 2005/0147201 A1 Jul. 7, 2005

(51) Int. Cl.
*H01J 35/24* (2006.01)
(52) U.S. Cl. .............................. 378/15; 378/4; 378/19; 378/134; 378/137
(58) Field of Classification Search ................ 378/9, 378/4, 11, 15, 13, 19, 98.8, 98.2, 210; 250/370.09
See application file for complete search history.

(56) References Cited

U.S. PATENT DOCUMENTS

| | | | |
|---|---|---|---|
| 5,218,533 A * | 6/1993 | Schanen ......................... 378/9 |
| 5,224,136 A * | 6/1993 | Toth et al. ...................... 378/4 |
| 5,799,057 A | 8/1998 | Hoffman et al. |
| 5,901,197 A * | 5/1999 | Khutoryansky et al. ...... 378/15 |
| 6,067,342 A * | 5/2000 | Gordon ......................... 378/19 |
| RE37,536 E | 2/2002 | Barnes |
| 6,359,958 B2 | 3/2002 | Toth |
| 6,369,389 B1 | 4/2002 | Berland et al. |
| 6,385,279 B1 | 5/2002 | Toth et al. |
| 6,408,049 B1 | 6/2002 | Edic et al. |
| 6,448,566 B1 | 9/2002 | Riedner et al. |
| 6,479,824 B1 | 11/2002 | Hoffman |
| 6,480,562 B2 | 11/2002 | Jiang et al. |
| 6,480,563 B2 | 11/2002 | Hoffman et al. |
| 6,661,866 B1 | 12/2003 | Limkeman et al. |
| 6,760,399 B2 * | 7/2004 | Malamud ........................ 378/9 |
| 6,963,631 B2 * | 11/2005 | Brunnett .................... 378/98.8 |
| 6,980,623 B2 * | 12/2005 | Dunham et al. .............. 378/19 |
| 2003/0103666 A1 | 6/2003 | Edic et al. |
| 2005/0100132 A1 * | 5/2005 | Block et al. ................ 378/124 |

* cited by examiner

*Primary Examiner*—Edward J. Glick
*Assistant Examiner*—Ansstasia S. Midkiff
(74) *Attorney, Agent, or Firm*—Carl B. Horton, Esq.; Armstrong Teasdale LLP

(57) ABSTRACT

A method for scanning an object to reduce image degradation includes scanning the object in a helical mode using a multi-slice CT imaging system having a plurality of detector arrays arranged along a z-axis direction and a radiation source having a beam focal spot. The method further includes wobbling the focal spot of the radiation source in the z-axis direction during the scanning to selectively preferentially illuminate individual detector arrays through the scanned object for each view. Data is collected from each detector array for each view only when the detector array from which data is being collected is selectively illuminated.

22 Claims, 3 Drawing Sheets

MULTIDETECTOR CT IMAGING METHOD AND APPARATUS WITH REDUCING RADIATION SCATTERING

BACKGROUND OF THE INVENTION

This invention relates generally to computed tomographic (CT) imaging methods and apparatus and more particularly to CT methods and apparatus having a plurality of detector arrays.

At least one known CT imaging system utilizes a multi-slice detector array comprising a scintillator and a photo-diode arrays. Each detector array contains a plurality of detector cells that are used to measure attenuation information of an object for image back projection for a single or multiple slice planes through the patient. As used herein, a "detector cell" is the smallest portion of a detector array from which attenuation data can be obtained.

At least one known CT imaging system utilizes multi-energy scanning to differentiate tissues or materials having different densities. For example, CT imaging systems have been used to distinguish calcium and iodine in medical applications. One known method uses a single slice image obtained from a CT imaging system having a single detector system. Two different X-ray beam filters are used, or two different x-ray tube peak voltages are used with beams that exactly overlap spatially. The two different filters or tube voltages are applied at different times to obtain two images of the same volume. These two images are processed to separate material of varying densities. For example, in at least one known methods, processing involves image subtraction. A slice of data is be acquired at one x-ray tube peak voltage or using a first filter. Next, the x-ray tube peak voltage is changed or a filter at the x-ray tube is changed, or both, and a second slice of data is acquired at the same location of the imaged object. The two slices of data are be processed to separate materials of varying densities within that slice plane, again usually by image subtraction. However, this process is complex and time consuming, and therefore has not gained wide acceptance among CT users.

In another known CT apparatus, a simpler dual energy or multi-energy detection process is used. However, direct conversion CT detectors, when utilized exclusively in a CT imaging apparatus, cannot count X-rays fast enough to support CT flux rates and scan times. Such detectors used in the current mode have high non-linearities that make it difficult to achieve artifact free scanning.

BRIEF DESCRIPTION OF THE INVENTION

There is therefore provided, in some aspects of the present invention, a method for scanning an object to reduce image degradation. The method includes scanning the object in a helical mode using a multi-slice CT imaging system having a plurality of detector arrays arranged along a z-axis direction and a radiation source having a beam focal spot. The method further includes wobbling the focal spot of the radiation source in the z-axis direction during the scanning to selectively preferentially illuminate individual detector arrays through the scanned object for each view. Data is collected from a detector array for each view only when the detector array from which data is being collected is selectively illuminated.

In other aspects of the present invention, a CT imaging apparatus is provided. The CT imaging apparatus includes a radiation source on a rotating gantry having a beam focal spot and a plurality of detector arrays arranged along a z-axis and configured to detect radiation from the radiation source passing through an object to be imaged. The CT imaging apparatus is configured to scan an object in a helical mode, wobble the focal spot of the radiation source in the z-axis direction during scanning to selectively preferentially illuminate individual the detector arrays through the scanned object for each view. Data is collected from a detector array for each view only when the detector array from which data is being collected is selectively illuminated.

DETAILED DESCRIPTION OF THE INVENTION

Figure 1:
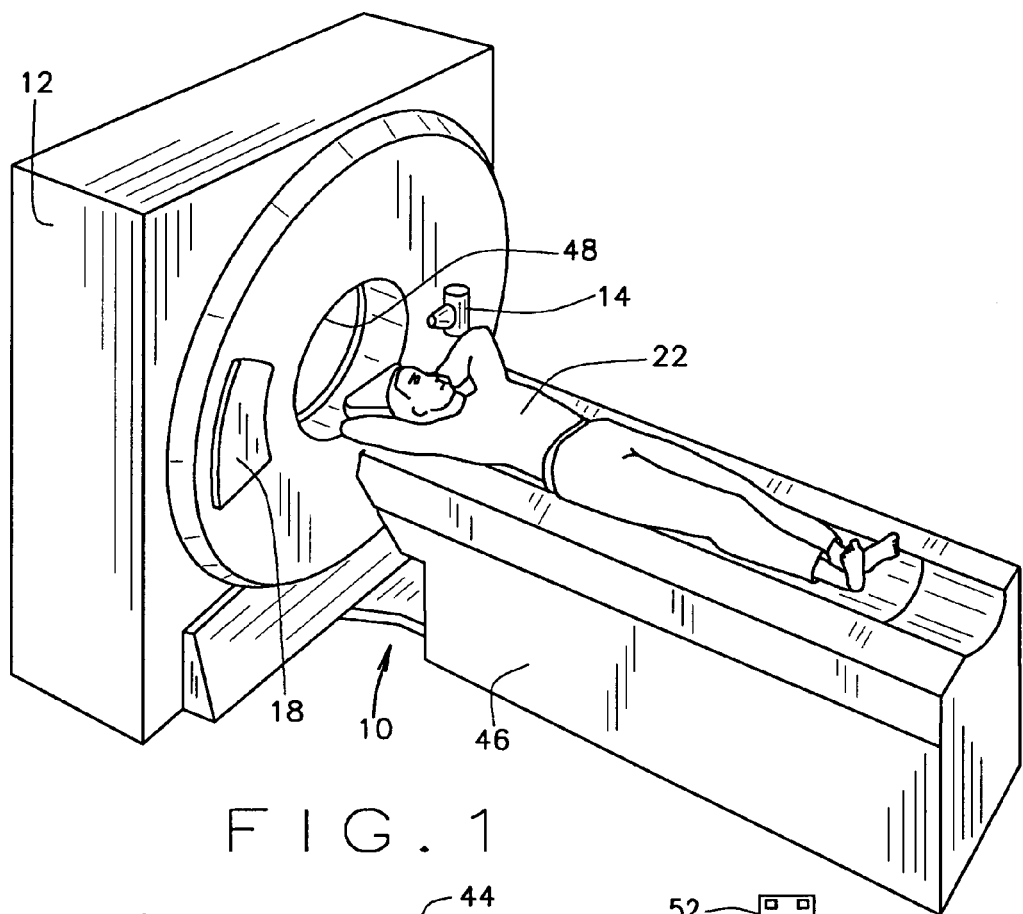
FIG. 1 is a pictorial drawing representative of some configurations of CT imaging apparatus of the present invention.

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as the filtered backprojection technique. This process converts the attenuation measurements from a scan into integers called "CT numbers" or "Hounsfield units" (HU), which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two-dimensional slice taken through the object.

To further reduce the total acquisition time, multi-slice CT has been introduced. In multi-slice CT, multiple rows of projection data are acquired simultaneously at any time instant. When combined with helical scan mode, the system generates a single helix of cone beam projection data. Similar to the single slice helical, weighting scheme, a method can be derived to multiply the weight with the projection data prior to the filtered backprojection algorithm.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 2:
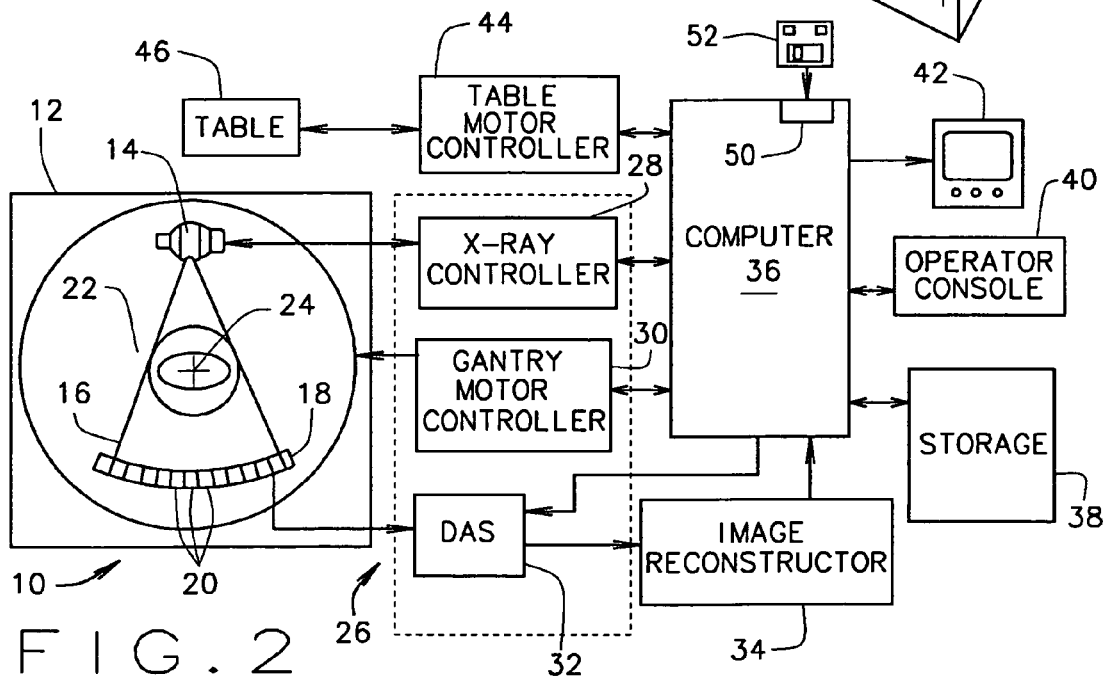
FIG. 2 is a functional block diagram representative of the CT imaging apparatus of FIG. 1.

Referring to FIGS. 1 and 2, a multi-slice scanning imaging system, for example, a Computed Tomography (CT) imaging system 10, is shown as including a gantry 12 representative of a "third generation" CT imaging system. Gantry 12 has a radiation source 14, for example, an x-ray tube (also called an x-ray source herein) that projects a beam of radiation 16 such as x-rays toward a detector array 18 on the opposite side of gantry 12. Detector array 18 is formed by a plurality of detector rows (not shown) including a plurality of detector elements or "cells" 20 that together sense the projected radiation that passes through an object, such as a medical patient 22 between array 18 and source 14. Each detector element 20 produces an electrical signal that represents the intensity of an impinging radiation beam and hence can be used to estimate the attenuation of the beam as it passes through object or patient 22. During a scan to acquire radiation projection data, gantry 12 and the components mounted therein rotate about a center of rotation 24, and the rotation defines a z-axis of imaging system 10. FIG. 2 shows only a single row of detector elements 20 (i.e., a detector row). However, a multi-slice detector array 18 includes a plurality of parallel detector rows of detector elements 20 such that projection data corresponding to a plurality of quasi-parallel or parallel slices can be acquired simultaneously during a scan. Moreover, configurations of the present invention include a plurality of detector arrays, as explained in more detail below.

Rotation of components on gantry 12 and the operation of radiation source 14 are governed by a control mechanism 26 of CT system 10. Control mechanism 26 includes an radiation controller 28 such as an x-ray controller that provides power and timing signals to radiation source 14 and a gantry motor controller 30 that controls the rotational speed and position of components on gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38. Image reconstructor 34 can be specialized hardware or computer programs executing on computer 36.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, radiation controller 28, and gantry motor controller 30. In addition, computer 36 operates a table motor controller 44, which controls a motorized table 46 to position patient 22 in gantry 12. Particularly, table 46 moves portions of patient 22 through gantry opening 48. The direction of movement is in a z-axis direction.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or another digital source such as a network or the Internet, as well as yet to be developed digital means. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. Although the specific embodiment mentioned above refers to a third generation CT system, the methods described herein equally apply to fourth generation CT systems (stationary detector—rotating radiation source) and fifth generation CT systems (stationary detector and radiation source). Additionally, it is contemplated that the benefits of the invention accrue to imaging modalities other than CT. Additionally, although the herein described methods and apparatus are described in a medical setting, it is contemplated that the benefits of the invention accrue to non-medical imaging systems such as those systems typically employed in an industrial setting or a transportation setting, such as, for example, but not limited to, a baggage scanning system for an airport or other transportation center.

Figure 3:
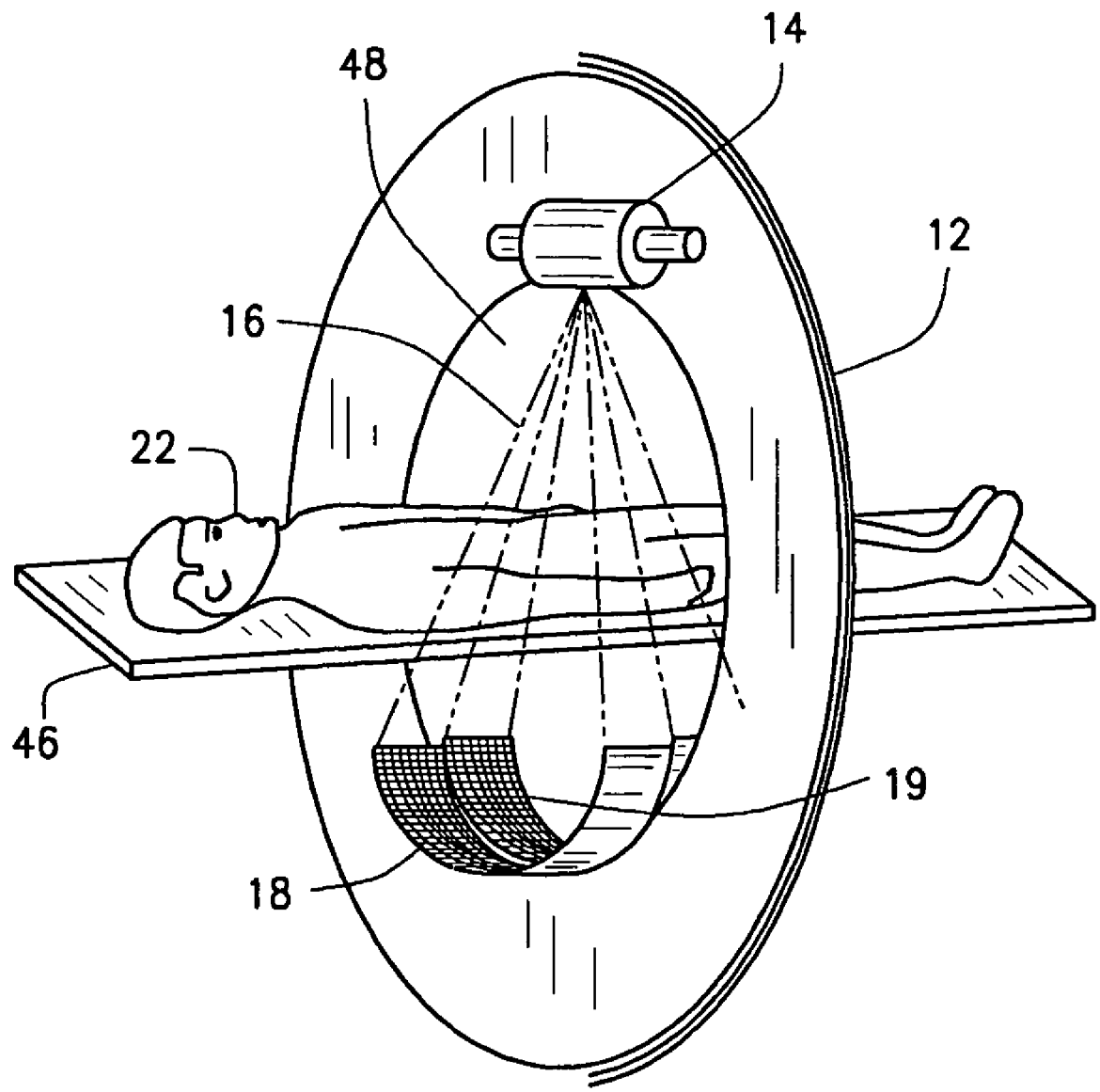
FIG. 3 is a simplified cut-away pictorial diagram representative of a portion of the CT imaging apparatus of FIGS. 1 and 2, and of various dual-detector configurations of the present invention.

When a multi-slice CT imaging system such as imaging system 10 is used in a helical mode, adjacent slice planes through an object 22 are viewed by multiple detector cells 20 in the z-axis direction at successive points in time, if the rotational pitch is appropriately wide (e.g., at least one detector cell wide). In some configurations of the present invention and referring to FIG. 3, at least two separate detector arrays 18 and 19, which may be of different types, are arranged along a z-axis direction, for example, adjacent each other along the z-axis direction. In this manner, adjacent slice planes through an object 22 can be viewed by each detector array 18, 19 at slightly different times, dependent upon the scan pitch. A first detector array 18 having conventional scintillator/photo-sensor elements or cells 20 is provided in some configurations. First detector 18 collects attenuation data that is processed to create anatomical detail for CT slices. In some configurations, a second detector array 19 having detector elements 20 different from that of detector array 18 is also provided. For example, a direct conversion detector array 19 is provided that is configured to acquire x-ray count and energy data. Detectors of this type are currently used in CT-Bone Mass Detection (CT-BMD) systems and Gamma camera systems. The information acquired by second detector 19 is particularly useful for tissue differentiation and can be used to derive information about the composition and density of various tissue materials in medical CT or more generally to distinguish different compositions within a scanned object 22. This information would allow the discrimination of iodine, calcium, and other materials as well. For example, in medical applications, information from detectors arrays 18 and 19 can be super-positioned to create a single image with identically positioned and overlapping information with both anatomical detail and tissue discrimination (Material type and density) both.

In some configurations, direct conversion detector array 19 is a provided in single slice configuration, whereas in other configurations, direct conversion detector is provided in a multiple slice configuration. Multiple slice configurations can be used to provide information on a variety of different tissue materials or data from multiple slices. Direct conversion detector array 19 can also be integrated across multiple slices for improved statistics on an individual material. In some configurations, a scintillator/diode detector array 18 is provided adjacent to a direct conversion detector array 19 that is used in an x-ray counting and energy discrimination mode (See picture). This operational mode adds a small amount of additional dose to a CT exam of a patient 22 because only a fraction of x-ray radiation is needed for energy discrimination in comparison to conventional CT scanning.

The use of a plurality of detector arrays (e.g., detector arrays 18 and 19) allows the super position of anatomical detail and tissue characterization information on an image, as well as the measurement and correction for scatter. Direct conversion detector array 19 can be used to pre-measure patient 22 and to adjust x-ray tube 14 current within a slice and from slice to slice. Imaging systems 10 can use data from detector arrays 18 and 19 to implement CT corrections such as beam hardening and detector correction. Additionally, in some configurations, x-ray beam kVp is varied in the z-axis direction, or an X-ray attenuation material having a variable attenuation in the z-axis direction is provided either at the X-ray tube or at detector arrays 18 and 19. This variation can be used to enhance the collection of multi-energy x-ray information in the area of direct conversion detector array 19. Direct conversion detector array 19 data can then be processed to separate different densities of materials within a patient slice plane in a simple operational mode. Multiple multi-energy CT slices can be collected at the same time as standard CT slices, but in a different area of the anatomy. The multi-energy CT slices can be super-imposed at a later time to separate multiple types of materials.

In some configurations of the present invention, when detectors arrays 18 and 19 are operated simultaneously, scatter from a radiation beam 16 that falls on one detector array 18 or 19 is scattered. Radiation that scatters in the z-axis direction can cross over and degrade data being collected by the other detector array 19 or 18, respectively. Significant degradation occurs, for example, from scattering of a beam 16 impinging on scintillator/photo detector array 18 onto direct conversion energy discriminating detector array 19. This scattered radiation can adversely affect the ability of detector array 19 to count each x-ray and to measure its energy for the most effective use. In medical applications of imaging system 10, for example, this effect can be detrimental to tissue characterizations.

Some configurations of the present invention avoid the effect of scattered radiation cross-over from detector to detector by wobbling and/or dynamically controlling a focal spot of beam 16 in the z axis direction. As the focal spot is moved in the z-axis direction, some but not all configurations of the present invention also use radiation controller 28 to strobe or pulse radiation source 14. As object 22 is scanned in a helical mode using multi-slice CT imaging system 10, the focal spot is wobbled in the z-axis direction to selectively preferentially illuminate, through object 22, one detector of a plurality of detector arrays for each view. For example, in a configuration such as that represented in FIG. 3, detector array 18 is preferentially illuminated at a first time interval due to the wobbling of the focal spot. ("Selectively preferentially illuminated," as used herein, refers to the fact that radiation source 14 beams substantially more radiation in the direction of one of the detector arrays than towards the other or others.) Data is collected (i.e., acquired) from the selected detector array (in this case, detector array 20) only while it is preferentially illuminated. The radiation focal spot is then moved in the z-axis direction so that another detector (e.g., detector array 19) is selectively preferentially illuminated for a time interval. Data is collected for each view from each detector array 18 or 19 only when that detector is selectively preferentially illuminated.

In some configurations of the present invention, radiation controller 28 also strobes radiation source 14 so that radiation source 14 is off when the focal spot is wobbled between positions in which individual detector arrays are selectively preferentially illuminated. Radiation source 14 is turned on when the focal spot is in these positions so that data can be collected from the illuminated detector array. By pulsing radiation source 14 in this manner, the radiation dose received by a patient or object 22 is reduced or minimized. The focal spot is moved and pulsed for each detector for each view during a scan rotation. Each detector array 18, 19 of the plurality of detector arrays collects data only during the appropriate time in configurations in which radiation source 14 is pulsed.

Figure 4:
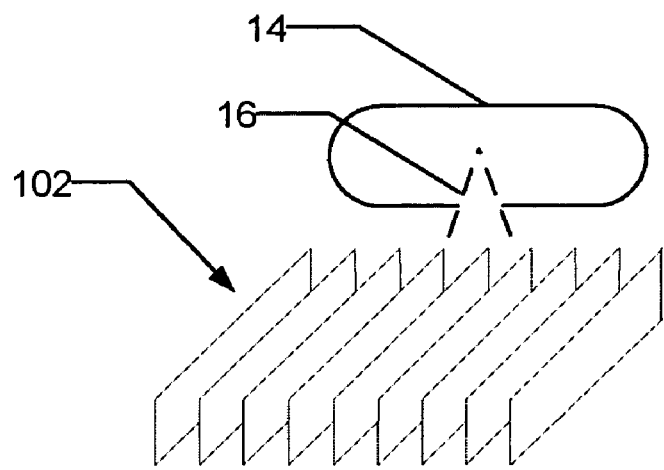
FIG. 4 is a drawing of an x-ray source and a pre-patient collimator.
Figure 5:
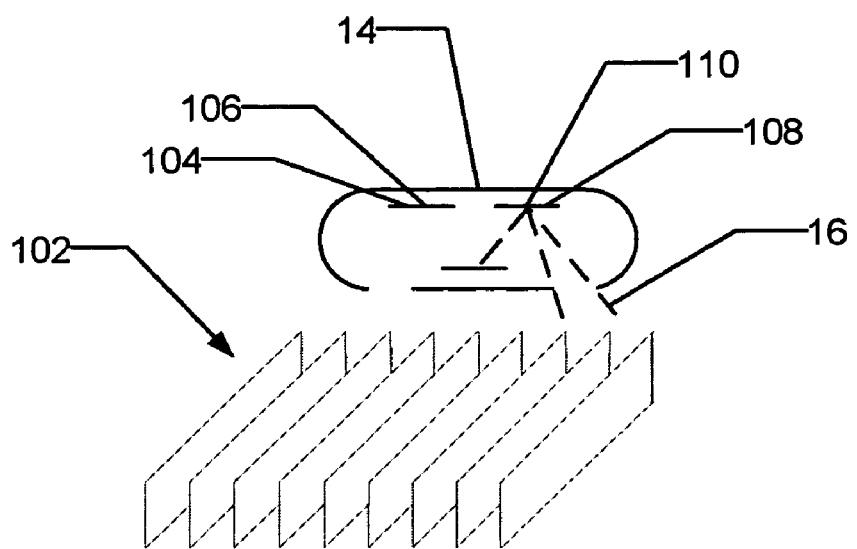
FIG. 5 is a drawing of an x-ray source having two cathodes and two focal spots.

In other configurations, and particularly in configurations in which beam motion is rapid, sufficient beam separation is provided from beam motion. Referring to FIG. 5, focal spot wobbling can be provided using a radiation source such as an x-ray tube 14 that has a dynamically (i.e., electrically) controlled focal spot 106, 110 in conjunction with a fixed pre-object or pre-patient collimator 102. In such configurations, radiation controller 28, in conjunction with computer 36, can be utilized to provide a wobble signal to x-ray tube 14. In some configurations, a pre-object or pre-patient collimator is moved to provide an effective wobbling of the focal spot of radiation source 14 in a z-axis direction. As shown in FIG. 4, a pre-object or pre-patient collimator 102 can be provided adjacent to or as part of x-ray source 14, as movable blades that are opaque to radiation from source 14. These blades are moved to ensure that radiation from source 14 is directed in a desired direction. In still other configurations, focal spot wobbling is accomplished by a combination of the movement of a pre-object or pre-patient collimator and dynamic control of the focal spot. At least two techniques can be used to achieve focal spot wobbling at x-ray source 14. In one technique, a steerable electron beam is used in conjunction with a single x-ray tube cathode to wobble the focal spot. In another technique and referring to FIG. 5, an x-ray tube is provided with two cathodes 104, 108 that are alternately strobed to illuminate two different focal spots 106, 110. Either of these techniques can be used in conjunction with a pre-object or pre-patient collimator that moves as described above.

Configurations of the present invention can be used to obtain super-position of anatomical detail and tissue characterization information. Also, the scattering of radiation can be measured and its effects compensated. In some configurations in which a direct conversion detector array is provided, this detector array can be used to pre-measure a patient and adjust system ma within a slice and from slice to slice. Smart CT correction can be provided using beam hardening or smart detector correction techniques. Tissue discrimination data obtained from multiple detector array configurations can be used to provide diagnostic information that is indicative of disease processes. This discrimination data may include detection of calcium in plaque, which may be indicative of stability of instability, and the amount and presence of iodine, which can be used to show flow through vessels, etc.

By reducing or avoiding the detrimental effects of radiation scattering, configurations of the present invention increases the ability of imaging system 10 to detect different materials and to characterize different tissues. Image quality is also improved for each detection system.

While the invention has been described in terms of various specific embodiments, those skilled in the art will recognize that the invention can be practiced with modification within the spirit and scope of the claims.

What is claimed is:

1. A method for scanning an object to reduce image degradation, said method comprising:
    scanning the object in a helical mode using a multi-slice CT imaging system having a plurality of detector arrays arranged along a z-axis direction, said z-axis direction being along a scanning direction of a longitudinal axis of a patient, and a radiation source having a beam focal spot;
    controlling a wobble of the focal spot of the radiation source in the z-axis direction during said scanning to selectively preferentially illuminate individual said detector arrays through the scanned object for each view;
    collecting data from each said detector array for each view only when the detector array from which data is being collected is selectively illuminated.

2. A method in accordance with claim 1 wherein said controlling a wobble of the focal spot of the radiation source comprises moving a pre-object collimator.

3. A method in accordance with claim 2 wherein the radiation source is an x-ray tube, and controlling a wobble of the focal spot of the radiation source wobbling comprises dynamically controlling the x-ray tube focal spot.

4. A method in accordance with claim 3 wherein dynamically controlling the x-ray tube focal spot comprises steering an electron beam to illuminate two focal spots of a cathode of the x-ray tube.

5. A method in accordance with claim 3 wherein dynamically controlling the x-ray tube focal spot comprises alternately strobing two cathodes in an x-ray tube to illuminate two different focal spots.

6. A method in accordance with claim 1 wherein said controlling a wobble of the focal spot of the radiation source comprises dynamically controlling the radiation tube focal spot.

7. A method in accordance with claim 1 wherein said object is a medical patient.

8. A method for scanning an object to reduce image degradation, said method comprising:
    scanning the object in a helical mode using a multi-slice CT imaging system having a plurality of detector arrays arranged along a z-axis direction, said z-axis direction being along a scanning direction of a longitudinal axis of a patient, and a radiation source having a beam focal spot;
    controlling a wobble of the focal spot of the radiation source in the z-axis direction during said scanning to selectively preferentially illuminate individual said detector arrays through the scanned object for each view;
    pulsing the radiation source so that the radiation source is off when the focal spot is wobbled between positions in which individual said detector arrays are selectively preferentially illuminated; and
    collecting data from each said detector array for each view only when the detector array from which data is being collected is selectively illuminated.

9. A method in accordance with claim 8 wherein said controlling a wobble of the focal spot of the radiation source comprises moving a pre-object collimator.

10. A method in accordance with claim 9 wherein the radiation source is an x-ray tube, and said controlling a wobble of the focal spot of the radiation source comprises dynamically controlling the x-ray tube focal spot.

11. A method in accordance with claim 8 wherein said controlling a wobble of the focal spot of the radiation source comprises dynamically controlling the radiation tube focal spot.

12. A CT imaging apparatus comprising:
    a radiation source on a rotating gantry having a beam focal spot; and
    a plurality of detector arrays arranged along a z-axis, said z-axis direction being along a scanning direction of a longitudinal axis of a patient, and configured to detect radiation from said radiation source passing through an object to be imaged;
    said CT imaging apparatus configured to:
    scan an object in a helical mode;
    control a wobble of the focal spot of the radiation source in said z-axis direction during said scanning to selectively preferentially illuminate individual said detector arrays through the scanned object for each view; and
    collect data from each said detector array for each view only when the detector array from which data is being collected is selectively illuminated.

13. An apparatus in accordance with claim 12 further comprising a moveable pre-object collimator, and to control a wobble of the focal spot of the radiation source, said apparatus is configured to move said pre-object collimator.

14. An apparatus in accordance with claim 13 wherein said radiation source is an x-ray tube, and to control a wobble of the focal spot of the radiation source, said apparatus is further configured to dynamically control the x-ray tube focal spot.

15. An apparatus in accordance with claim 14 wherein to dynamically control the x-ray tube focal spot, said apparatus is configured to steer an electron beam of the x-ray tube to illuminate two different focal spots of a single cathode.

16. An apparatus in accordance with claim 14 wherein said x-ray tube comprises two cathodes, and to dynamically control the x-ray tube focal spot, said apparatus is configured to alternately strobe focal spots of the two different cathodes.

17. An apparatus in accordance with claim 12 wherein to control a wobble of the focal spot of the radiation source, said apparatus is further configured to dynamically control the radiation source focal spot.

18. An apparatus in accordance with claim 12 further comprising a movable table configured to support a patient between said radiation source and said detector arrays.

19. A CT imaging apparatus comprising:
a radiation source on a rotating gantry having a beam focal spot; and
a plurality of detector arrays arranged along a z-axis, said z-axis direction being along a scanning direction of a longitudinal axis of a patient, and configured to detect radiation from said radiation source passing through an object to be imaged;
said CT imaging apparatus configured to:
scan an object in a helical mode;
control a wobble of the focal spot of the radiation source in said z-axis direction during said scanning to selectively preferentially illuminate individual said detector arrays through the scanned object for each view;
pulse the radiation source so that the radiation source is off when the focal spot is wobbled between positions in which each of said detector arrays is selectively preferentially illuminated; and
collect data from each said detector array for each view only when the detector array from which data is being collected is selectively illuminated.

20. An apparatus in accordance with claim 19 further comprising a moveable pre-object collimator, and to control a wobble of the focal spot of the radiation source, said apparatus is configured to move said pre-object collimator.

21. An apparatus in accordance with claim 20 wherein said radiation source is an x-ray tube, and to control a wobble of the focal spot of the radiation source, said apparatus is further configured to dynamically control the x-ray tube focal spot.

22. An apparatus in accordance with claim 19 wherein to control a wobble of the focal spot of the radiation source, said apparatus is further configured to dynamically control the radiation source focal spot.

* * * * *

UNITED STATES PATENT AND TRADEMARK OFFICE
CERTIFICATE OF CORRECTION

PATENT NO. : 7,187,748 B2  Page 1 of 1
APPLICATION NO. : 10/748612
DATED : March 6, 2007
INVENTOR(S) : Hoffman It is certified that error appears in the above-identified patent and that said Letters Patent is hereby corrected as shown below:

In Claim 3, column 7, line 56, between "and" and "controlling" insert --said--.

Signed and Sealed this

Nineteenth Day of August, 2008

JON W. DUDAS
*Director of the United States Patent and Trademark Office*